(12) United States Patent
Baetz et al.

(10) Patent No.: US 8,792,617 B2
(45) Date of Patent: Jul. 29, 2014

(54) METHOD AND X-RAY SYSTEM TO CREATE A DUAL ENERGY X-RAY IMAGE

(75) Inventors: Lothar Baetz, Heroldsberg (DE); Mathias Hoernig, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/410,563

(22) Filed: Mar. 2, 2012

(65) Prior Publication Data

US 2012/0224668 A1 Sep. 6, 2012

(30) Foreign Application Priority Data

Mar. 3, 2011 (DE) .......................... 10 2011 005 055

(51) Int. Cl.
*H05G 1/64* (2006.01)
(52) U.S. Cl.
USPC ........................................ 378/98.11; 378/16
(58) Field of Classification Search
USPC ......... 378/5, 21, 22, 98.9, 9, 16, 98.11, 98.12
See application file for complete search history.

(56) References Cited

U.S. PATENT DOCUMENTS

| | | | | |
|---|---|---|---|---|
| 4,149,081 A | * | 4/1979 | Seppi | 250/445 |
| 4,561,054 A | * | 12/1985 | Andrews et al. | 364/414 |
| 4,662,379 A | * | 5/1987 | Macovski | 378/5 |
| 4,686,695 A | * | 11/1987 | Macovski | 378/146 |
| 4,780,897 A | * | 10/1988 | McDaniel et al. | 378/62 |
| 6,320,931 B1 | | 11/2001 | Arnold | |
| 6,683,934 B1 | | 1/2004 | Zhao et al. | |
| 6,931,098 B2 | * | 8/2005 | Kump et al. | 378/98.9 |
| 6,950,493 B2 | * | 9/2005 | Besson | 378/16 |
| 7,116,749 B2 | * | 10/2006 | Besson | 378/16 |
| 7,352,885 B2 | | 4/2008 | Eberhard et al. | |
| 2005/0243970 A1 | | 11/2005 | Bernhardt | |
| 2006/0067473 A1 | * | 3/2006 | Eberhard et al. | 378/98.9 |
| 2008/0144767 A1 | * | 6/2008 | Eberhard et al. | 378/22 |
| 2008/0198963 A1 | * | 8/2008 | Spahn | 378/5 |
| 2009/0161815 A1 | * | 6/2009 | Grass et al. | 378/5 |
| 2010/0020920 A1 | * | 1/2010 | Mertelmeier | 378/9 |
| 2010/0119035 A1 | | 5/2010 | Karch | |

\* cited by examiner

*Primary Examiner* — Hoon Song
(74) *Attorney, Agent, or Firm* — Schiff Hardin LLP

(57) ABSTRACT

In a method to create dual energy x-ray image data of a predetermined volume segment of an examination subject with an x-ray system, a low-energy x-ray image data of the volume segment is created, a high-energy x-ray image data of the volume segment is created, the low-energy x-ray image data is subtracted from the high-energy x-ray image data to create the dual energy x-ray image data. An x-ray filter that consists essentially of titanium is used in the creation of the dual energy x-ray image data.

18 Claims, 2 Drawing Sheets

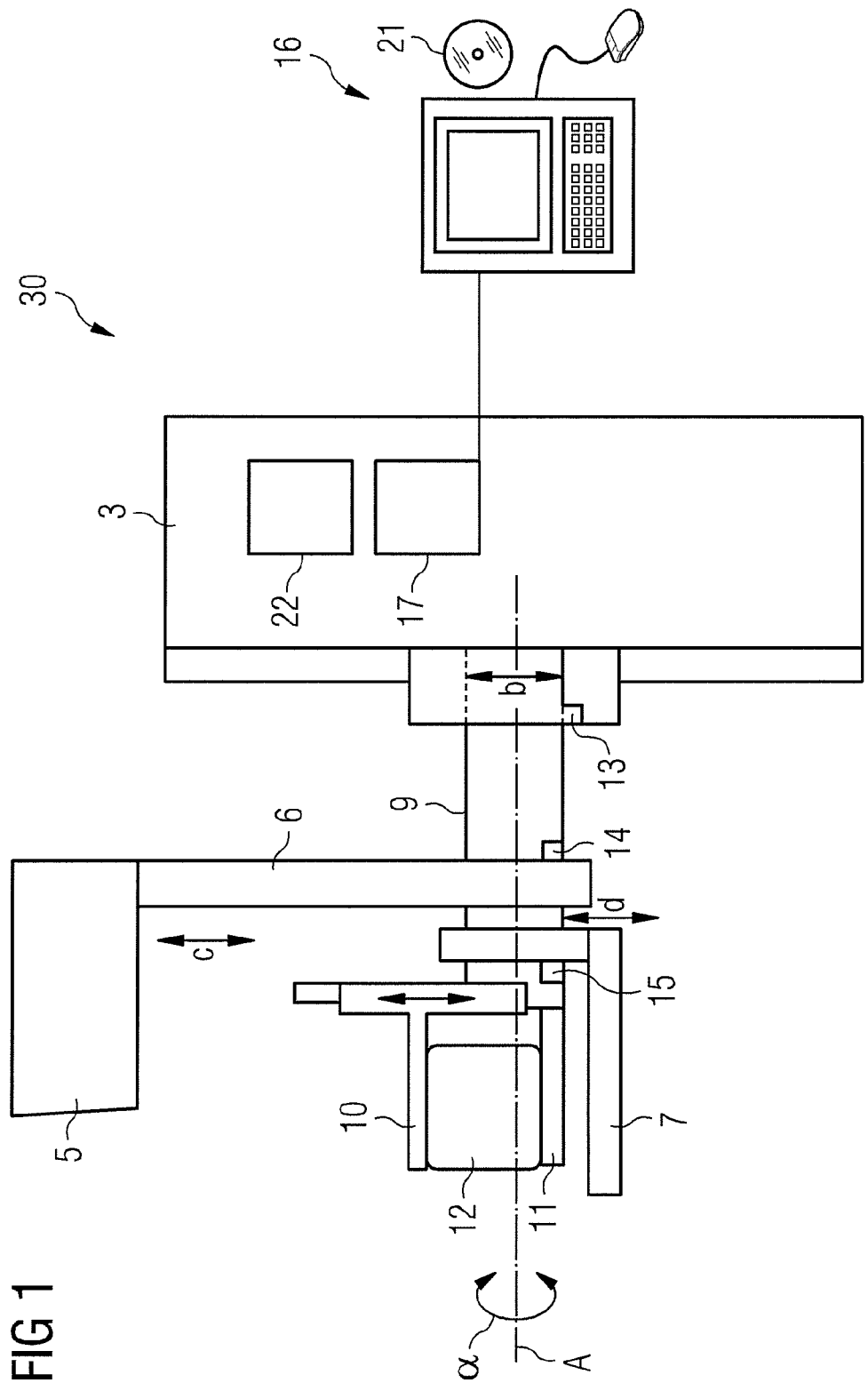

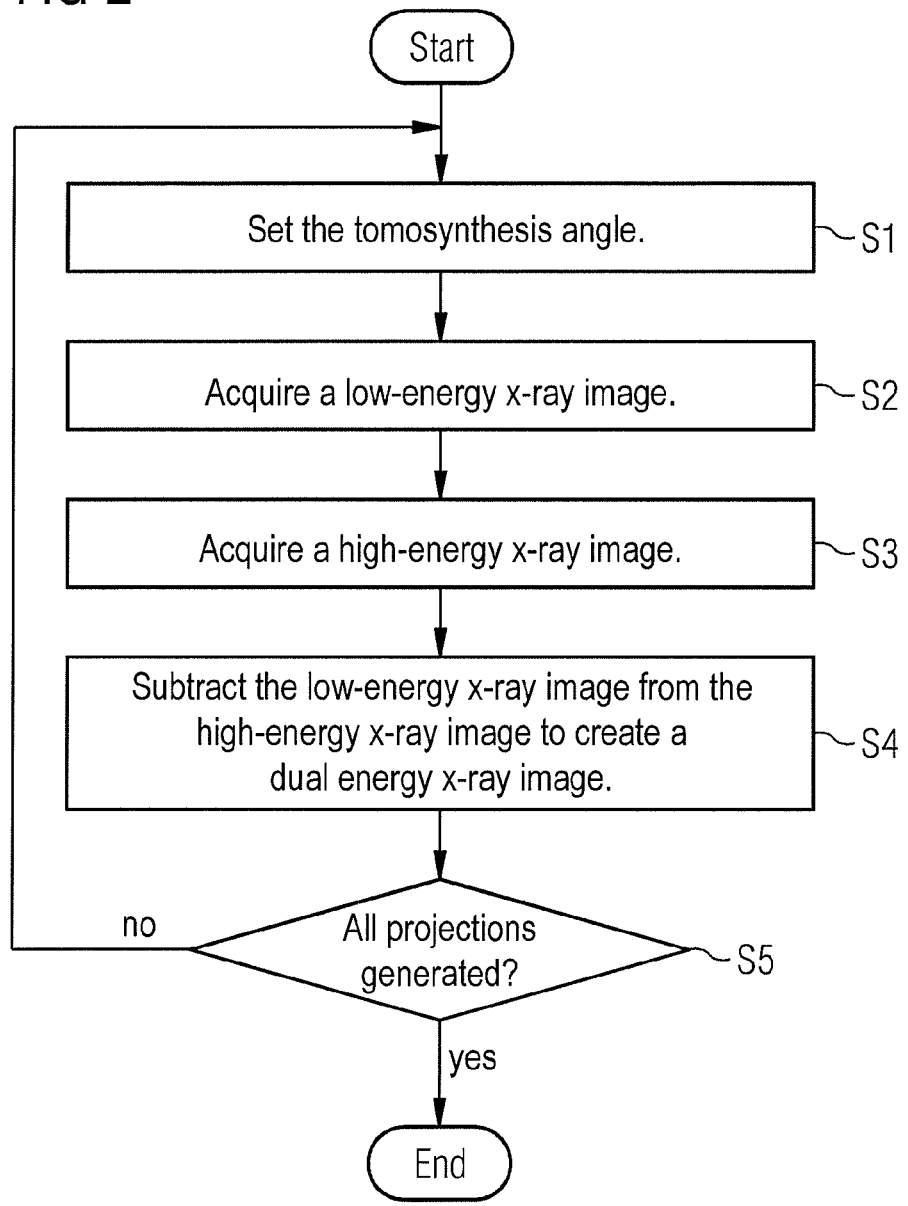

METHOD AND X-RAY SYSTEM TO CREATE A DUAL ENERGY X-RAY IMAGE

BACKGROUND OF THE INVENTION

1. Field of the Invention

The present invention concerns a method to create x-ray images using two different energy spectra ("dual energy"), known as dual energy x-ray images, as well as an x-ray system designed to create dual energy x-ray images.

2. Description of the Prior Art

U.S. Pat. No. 6,683,934 B1 describes a method to create dual energy x-ray images in mammography, wherein an x-ray filter made of copper (Cu) that is 0.25 mm thick is used for the high-energy images and an x-ray filter made of aluminum (Al) that is 2 mm thick is used for the low-energy images.

US 2005/0243970 A1 describes an x-ray system for use in mammography. A special x-ray filter is used in order to reduce a radiation exposure of the patient.

In order to be able to better show a tumor or a lesion in an x-ray image, it is known to inject a contrast agent (iodine, for example) into a patient to be examined. Particularly, in the case of malignant tumors, an enrichment of the contrast agent in the tumor takes place due to the neovascularization. For presentation, according to the prior art a dual energy imaging is used, wherein a low-energy image (x-ray voltage in a range from 20 to 35 kVp) and a high-energy image (x-ray voltage in a range from 40 to 50 kVp) are created from the same volume segment. The low-energy image (in which the contrast agent is not perceptible, or is nearly imperceptible) is subsequently subtracted from the high-energy image (in which the contrast agent is better visible).

Dual energy imaging, also known as the two spectra method, is used in mammography in order to achieve an improved diagnosis for the radiologist as well as an improvement of the sensitivity and specificity. An x-ray system to create dual energy x-ray images must satisfy the following conditions as well as possible, in particular in the creation of the high-energy images:

An optimal quantum yield should be achieved.
The high-energy images should exhibit an optimally high contrast-to-noise ratio.
The x-ray dose used to create the high-energy images should be as low as possible.

SUMMARY OF THE INVENTION

An object of the present invention is to satisfy the conditions stated above in the generation of the dual energy x-ray image better than is achieved according to the prior art.

This object is achieved in accordance with the invention by a method to create a dual energy x-ray image of a predetermined volume segment of an examination subject (a patient, for example) with an x-ray system, in which the low-energy x-ray image data of the predetermined volume segment are obtained, high-energy x-ray image data of the predetermined volume segment are obtained, the low-energy x-ray image data are subtracted from the high-energy x-ray image data, wherein the resulting difference image data being used to create the dual energy x-ray image data, or correspond to the dual energy x-ray image data.

In accordance with the invention, the generation of the dual energy x-ray image data, an x-ray filter is used that essentially consists of titanium (Ti).

The x-ray radiation generated by the x-ray source of the x-ray system is filtered with an x-ray filter before it strikes the predetermined volume segment. The x-ray filter has the task of optimizing the beam quality of the x-ray radiation in order to maximize the image quality per absorbed x-ray dose. Generally, an optimal (i.e. most mono-energetic) radiation exists for every task (for example the discovery of microcalcifications, or for the discovery of tumors in a given subject of a given thickness). Through the x-ray filter that is used, it is sought to modify the beam quality of the x-ray radiation striking the predetermined volume segment such that this x-ray radiation corresponds as much as possible to the optimal radiation.

Within the scope of the present invention, the x-ray filter consists essentially of titanium and an x-ray filter comprising at least 90%—preferably 95%, more preferably 99%, and more preferably 100% (% by weight)—titanium. The x-ray filter according to the invention is optimally produced exclusively from titanium (except for the unintentional impurities in the manufacture), or it can be produced from a titanium alloy that consists essentially of titanium.

X-ray image data according to the invention are data representing two-dimensional x-ray images and data representing three-dimensional x-ray images as well (three-dimensional x-ray image data, or three-dimensional x-ray information). For example, a slice in the three-dimensional x-ray image data corresponds to a two-dimensional x-ray image. This applies to the dual energy x-ray image data, to the low-energy x-ray image data and to the high-energy x-ray image data.

The subtraction (subtraction procedure) of the low-energy image data from the high-energy image data normally also includes a registration of the low-energy image data with the high-energy image data, such that corresponding image data elements (pixels, for example) are subtracted in the actual subtraction. Moreover, the subtraction procedure can also include a weighting so that the corresponding low-energy image data and/or high-energy image data are multiplied by a corresponding coefficient before the actual subtraction. In a special case, this coefficient can be negative, such that in this event the subtraction would actually be an addition.

The use of an x-ray filter consisting essentially of titanium according to the invention to create the dual energy x-ray image means that this x-ray filter can be used either to create the high-energy x-ray image, or to create the low-energy x-ray image, or can be used both to create the high-energy x-ray image and to create the low-energy x-ray image. If the x-ray filter consisting essentially of titanium is used only to create the high-energy x-ray image or only to create (low-energy x-ray image), according to the invention a different x-ray filter which, for example, does not essentially consist of titanium (but rather is composed of molybdenum (Mo) or rhodium (Rh)) can be used to create the low-energy x-ray image (or the high-energy x-ray image).

In the event that the x-ray filter consisting essentially of titanium is used to create the high-energy x-ray image, the thickness of this x-ray filter is preferably between 1 mm and 1.5 mm. Given use of an energy of up to 49 kV$_p$, a thickness of the x-ray filter of 1.3 mm is appropriate. Given use of a contrast agent including iodine, the tube voltage is preferably between 45 and 50 kV$_p$.

An x-ray filter consisting essentially of titanium can also be used to create the low-energy x-ray image. If an x-ray voltage in a range between 23 kVp and 35 kVp is used to create the low-energy x-ray image, the x-ray filter should have a thickness between 0.1 mm and 1 mm.

It is also possible for the same x-ray filter consisting of titanium to be used both to create the high-energy image and to create the low-energy image, in which case the x-ray filter has a thickness of 0.5 to 1.2 mm, and preferably approximately 1 mm.

The use of the same x-ray filter both in the generation of high-energy images and in the generation of low-energy images has the significant advantage that a filter change which takes at least 2 s (even in newer x-ray systems) is not needed. Depending on the number of filter changes that are required for an acquisition sequence, an advantage in the range of minutes results from this with regard to a time duration that is necessary to create sequence composed of multiple dual energy x-ray images.

In a preferred embodiment of the invention, within the scope of a tomosynthesis scan multiple dual energy x-ray images of the predetermined volume segment (a female breast, for example) are created according to the invention. A high-energy x-ray image and a low-energy x-ray image are respectively created in the tomosynthesis scan for each tomosynthesis angle setting. The low-energy x-ray image created for the respective tomosynthesis angle setting is subsequently subtracted from the high-energy x-ray image created for this same tomosynthesis angle setting in order to generate the dual energy x-ray image to be created for this tomosynthesis angle setting.

The tomosynthesis can be digital tomosynthesis, which is a combination of a digital image acquisition and image processing given a slight movement of the x-ray tube or x-ray source through successive angle positions. Tomosynthesis has certain similarities to computed tomography (CT) but is considered a separate technique. While images are created during a complete 360° rotation of the x-ray source around the examination subject in computed tomography, in tomosynthesis the x-ray source pans only around a small angle of 40°, for example (typically between 10° and 60°), and only a small number of exposures (typically between 7 and 60) are created. Via the use of high-resolution detectors, a very high resolution can be achieved in planes perpendicular to the Z-axis (axis in the direction of the tomosynthesis angle 0° or vertical direction or CC alignment (Cranial Caudal (from head to foot))), even when the resolution in the direction of the Z-axis is lower. The primary field of use of tomosynthesis is the imaging of the female breast as a supplement to or substitute for mammography. In comparison to mammography, tomosynthesis operates with a lower radiation energy per projection. For example, given the same energy of the individual x-ray photons the total dose (Average Glandular Dose) (i.e. the sum of the radiation energy absorbed in the breast per unit of mass which is required to create all projections of a tomosynthesis) of the tomosynthesis corresponds to one to two times the dose to create one two-dimensional image.

In particular, there are two possibilities in the generation of the multiple dual energy x-ray images for the tomosynthesis scan:

1. All high-energy images are generated before or—even better—after all low-energy images have been generated.
2. One high-energy image, one low-energy image, one high-energy image etc. are respectively generated in alternation. Two variants of this possibility exist. In the first variant, the corresponding high-energy x-ray image and the corresponding low-energy x-ray image are created for each angle setting before the next tomosynthesis angle setting is set. In the second variant, the movement of the x-ray source takes place continuously, such that the tomosynthesis angle setting of a high-energy image does not entirely correspond to the tomosynthesis angle setting of the corresponding low-energy image.

While the x-ray filter must only be changed once in the first possibility, in the second possibility the x-ray filter must be changed virtually as often as the number of x-ray images to be created, such that in the second possibility the use of the same x-ray filter that is possible according to the invention in both the generation of the high-energy images and the generation of the low-energy images is clearly advantageously significant.

Since the time interval between a first point in time at which the corresponding low-energy image was created for a tomosynthesis angle setting and a second point in time at which the corresponding high-energy image was created for the same tomosynthesis angle setting is significantly shorter in the second possibility that in the first possibility, the probability that the volume segment has disadvantageously moved between the first point in time of the second point in time is significantly smaller given the second possibility than given the first possibility, such that the registration of the corresponding low-energy image with the corresponding high-energy image is normally significantly simpler to produce given the second possibility that is the case given the first possibility. Expressed differently, the quality of the dual energy imaging given the second possibility is normally higher than given the first possibility, such that according to the invention the (second) possibility preferred according to the prior art is improved with regard to its implementation time due to be spared filter change.

There are multiple possibilities to create the two-dimensional dual energy x-ray images starting from the low-energy images and high-energy images. A low-energy image and a corresponding high-energy image can be (registered and then) subtracted. However, it is also possible to create three-dimensional low-energy image data of the predetermined volume segment based on the low-energy images, and to create three-dimensional high-energy image data of the predetermined volume segment in the same manner from the high-energy images. The three-dimensional low-energy image data are then subsequently (registered and) subtracted from the three-dimensional high-energy image data in order to obtain three-dimensional dual energy image data of the predetermined volume segment. A slice of this two-dimensional dual energy image data then corresponds to a two-dimensional dual energy x-ray image.

Moreover, it is noted that the creation of a low-energy image and a high-energy image for the same tomosynthesis angle setting can also take place simultaneously. For this, an energy-discriminating x-ray detector is used which can differentiate between low-energy quanta and high-energy quanta. In other words, with such an x-ray detector both the low-energy image and the high-energy image can be created simultaneously with one generation of x-rays (with one shot), wherein most often that x-ray voltage which is necessary to create the high-energy image is selected as the x-ray voltage.

Within the scope of the present invention, an x-ray system with a detector, an x-ray filter and an x-ray source is also provided in order to emit x-rays directed towards the detector. In addition to the x-ray filter, an examination subject can be positioned between the x-ray source and the detector such that the x-rays first traverse the x-ray filter and subsequently traverse a predetermined volume segment of the examination subject before they strike the detector. The x-ray system has a controller to control the x-ray source and the detector, and an image computer in order to receive data of the predetermined volume segment that are acquired by the detector and to create dual energy x-ray image data. The x-ray system generates low-energy image data of the predetermined volume segment and high-energy image data of the predetermined volume segment, wherein a beam energy to create the high-energy image data is significantly higher than the beam energy to create the low-energy image data. The controller subtracts the low-energy image data from the high-energy image data with the aid of the image computer in order to generate the dual energy x-ray image data. The x-ray filter of the x-ray system consists essentially of titanium.

The advantages of the x-ray system according to the invention essentially correspond to the advantages of the method according to the invention as described above.

According to a preferred embodiment of the invention, the x-ray system is designed to implement a tomosynthesis, such that the x-ray system according to this embodiment can also be designated as a tomosynthesis apparatus.

The above object also is achieved in accordance with the present invention by a non-transitory, computer-readable data storage medium encoded with programming instructions, such as software, that cause any or all embodiments of the method described above to be implemented when the storage medium is loaded into a computerized control and evaluation system of an x-ray system.

The software can be source code (C++, for example) that must still be compiled (translated) and linked or that only must be interpreted, or it can be an executable software code that has only to be loaded into the corresponding computer for execution.

The electronically readable data medium can be, for example, a DVD, a magnetic tape, a memory card or a USB stick on which is stored electronically readable control information, in particular software as described above. All embodiments according to the inventive method described above can be implemented when this control information (software) is read from the data medium and stored in a controller or computer of an x-ray system.

The present invention has the following advantages compared to the prior art:

- An improved quantum yield of the x-ray radiation striking the examination subject is achieved via the use of the titanium x-ray filter.
- The service life of the x-ray tube is increased via the use of the titanium x-ray filter.
- The power requirements of an x-ray tube which occur given a tomosynthesis to create a dual energy imaging can better be met via the use of a titanium x-ray filter.
- The patient organ dose (i.e. the x-ray dose to which the organ of the patient is exposed) is reduced via the use of the titanium x-ray filter.
- The exchange of the x-ray filter in dual energy imaging is done away with via the use of the titanium x-ray filter.
- The dual energy imaging can be implemented more quickly.
- The workflow to create a dual energy imaging can thereby be optimized overall.
- The x-ray system is less complicated due to the lack of the presence of a filter change.
- The collimator of the x-ray system is less complex in its design due to the unnecessary filter change.
- The radiation exposure of the patient is reduced in conventional mammography applications via the titanium x-ray filter.
- In comparison to known arrangements (for example with anode material made of tungsten and an x-ray filter made of rhodium), the same image quality is achieved given use of a titanium x-ray filter in conventional mammography.

The present invention is in particular suitable to supplement or extend contrast agent-assisted mammography. Naturally, the present invention is not limited to this preferred field of application since dual energy x-ray images of other regions of the body of a living organism can also be presented with the present invention (even without prior contrast agent injection). The present invention is also suitable for dual energy imaging of in inanimate material, for example to examine pieces of luggage at an airport.

BRIEF DESCRIPTION OF THE DRAWINGS

FIG. 1 schematically illustrates an x-ray system according to the invention.

FIG. 2 is a flowchart for implementation of a tomosynthesis scan according to the invention.

DESCRIPTION OF THE PREFERRED EMBODIMENTS

An x-ray system 30 according to the invention (which can also be designated as a tomosynthesis apparatus) for mammography examinations is schematically shown in FIG. 1. The x-ray system 30 has a support arm 9 which is borne in a bearing such that it can pivot around a horizontally traveling axis A (see double arrow or, respectively angle α). The bearing is arranged on a stand 3 and can be adjusted vertically as indicated with the double arrow b. An arm 6 provided with an x-ray source 5, a flat panel detector 7 and a compression device consisting of a compression plate 10 and a bearing plate 11 are arranged on the support arm 9. In FIG. 1, a female breast 12 that is compressed by the compression plate 10 and the bearing plate 11 is shown in a schematic manner. The arm 6 can be pivoted around the axis A relative to the support arm 1, the detector 7 and the compression device 10, 11. Electric motors 13 through 15 of the x-ray system 30 are provided for height adjustments and pivot motions. An x-ray filter 1 is attached to the arm 6 between the x-ray source 5 and the compression device in order to filter the x-rays emitted by the x-ray source 5 before they strike the examination subject 12.

A control of the x-ray system 30 takes place via an operating device 16 of the x-ray system 30 which is connected with a controller 17 and an image computer 22 of the x-ray system 30. Specific methods (among them the method according to the invention) can be loaded into the controller 17 and the operating device 16 by means of a DVD 21.

In x-ray technology, the x-ray radiation is essentially bremsstrahlung with characteristic lines of the anode material (i.e. the material of the anode of the x-ray tube 5). In order to eliminate unwanted portions of the spectrum of the x-ray radiation emitted by the x-ray source 5 (for example low-energy radiation which only generates a dose but no contrast in the image to be created, or high-energy radiation which generates too low a contrast in the image to be created), an additional filtering is used in the form of the described x-ray filter 1. In general radiography, tungsten (W) is normally used as an anode material and aluminum (Al) or copper (Cu) are used for the x-ray filter. According to the prior art either molybdenum (Mo), rhodium (Rh) or tungsten (W) is used as an anode material in mammography, and the x-ray filter consists of either molybdenum (Mo) or rhodium (Rh).

Simulations of the present inventors have shown that a higher quality factor $CNR^2/D$ for a predetermined pixel area of the x-ray detector can be achieved given the creation of high-energy images with an x-ray voltage of approximately 49 kVp with an x-ray filter consisting of titanium than with x-ray filters consisting of copper. CNR (Contrast-to-Noise Ratio) thereby corresponds to the contrast-to-noise ratio, and D stands for the average absorbed tissue dose.

Comparison acquisitions with identical acquisition parameters that were implemented by the inventors also show an improved x-ray yield given a use of a 1 mm thick x-ray filter consisting of titanium in comparison to a 0.3 mm thick x-ray filter consisting of copper. These two-dimensional comparison exposures or high-energy images were respectively generated with an x-ray voltage of 47 kVp for a phantom. The high-energy images created with the x-ray filter consisting of titanium showed higher pixel signal values (and thus a better quantum yield) in comparison to the high-energy images created with the copper x-ray filter.

Moreover, the present inventors also implemented comparisons in the creation of low energy images. For this, low-energy images were created with an x-ray voltage of 28 kVp and a charge of 80 mAs with a 50 µm thick x-ray filter consisting of rhodium on the one hand, and with a 1 mm thick x-ray filter consisting of titanium on the other hand. Tungsten was thereby respectively used as an anode material. A respective measurement of the contrast-to-noise ratio showed comparable results.

In summary, the inventors thus established that an x-ray filter made of titanium of a thickness of 0.5 to 1.2 mm (best 1 mm) has advantages relative to the x-ray filters used according to the prior art given the generation of high-energy images, while the same x-ray filter made of titanium has no disadvantages relative to the x-ray filters used according to the prior art given the generation of low-energy images. Therefore, the use of a 1 mm thick x-ray filter made of titanium in the generation of dual energy images leads on the one hand to better results (since at least the high-energy images have a better quality), and on the other hand has the great advantage that no filter change must be implemented between the generation of a high-energy image and the generation of a low-energy image.

A workflow plan of a method according to the invention to generate multiple dual energy x-ray images in a tomosynthesis scan is shown in FIG. 2. A contrast agent is administered before the shown workflow.

In a first Step S1, the tomosynthesis angle alpha is set which remains constant for at least the acquisition of the next low-energy x-ray image and for the acquisition of the next high-energy x-ray image. A low-energy x-ray image is subsequently generated in Step S2 and a high-energy x-ray image is subsequently generated in Step S3. The low-energy x-ray image is subtracted from the high-energy x-ray image in Step S4 to create a dual energy x-ray image. This subtraction step S4 could also take place outside of the program loop S1 through S5, for example after the generation of all low-energy x-ray images and high-energy x-ray images, or temporally parallel to the creation of a subsequent low-energy x-ray images and high-energy x-ray images.

In Step S5, it is checked whether all projections (i.e. all low-energy and high-energy x-ray images required for the tomosynthesis scan) have been created. If this is not the case, the workflow branches to Step S1, in which the x-ray system 30 (in particular the arm 6) is set to the next tomosynthesis angle α and Steps S2 through S4 are repeatedly implemented in the manner described above. If it is detected in Step S5 that all projections necessary for the tomosynthesis scan have been created, the method ends.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to produce dual energy x-ray data representing a predetermined volume segment of an examination subject comprising:
    operating an x-ray system with an x-ray voltage in a range from 20 to 35 kVp to irradiate a subject with x-rays, while filtering said x-rays with a single filter consisting essentially of titanium and said single filter having a thickness in a range between 0.5 and 1.2 mm, to produce low-energy x-ray image data of a volume segment of the subject;
    also operating said x-ray system with an x-ray voltage in a range from 40 to 50 kVp to irradiate the subject with x-rays, while filtering said x-rays with said single filter consisting essentially of titanium and said single filter having a thickness in a range between 0.5 and 1.2 mm, to produce high-energy x-ray image data of said volume segment; and
    supplying said low-energy x-ray image data and said high-energy x-ray image data to a processor and, in said processor subtracting said low-energy x-ray image data from said high-energy x-ray image data to produce dual energy x-ray image data, and making said dual energy x-ray image data available in electronic form at an output of said processor.

2. A method as claimed in claim 1 wherein said x-ray system is an x-ray tomosynthesis system, and wherein said method comprises:
    operating said x-ray tomosynthesis system by implementing a tomosynthesis scan wherein said segment of said subject is irradiated with x-rays from a plurality of successive angle settings;
    for each of said angle settings, operating said x-ray tomosynthesis system to produce said low-energy x-ray image data and to produce said high-energy x-ray image data; and
    for each of said angle settings, producing a dual energy x-ray image by subtracting the low-energy x-ray image data produced at the respective angle setting from the high-energy x-ray image data produced at the respective angle setting.

3. A method as claimed in claim 2 comprising irradiating the volume segment of the subject with x-rays with said x-ray tomosynthesis image system to produce said low-energy x-ray image data and said high-energy x-ray image data for the respective angle setting before moving said x-ray tomosynthesis image system to a next successive angle setting.

4. A method as claimed in claim 1 wherein said x-ray image system is an x-ray tomosynthesis image system, and wherein said method comprises:
    operating said x-ray tomosynthesis image system in a tomosynthesis scan to produce said low-energy x-ray image data and said high-energy x-ray image data in alternation with continuous movement of said x-ray source in said tomosynthesis scan; and
    in said processor, subtracting respectively alternating low-energy x-ray image data from respectively alternating high-energy x-ray image data to produce said dual energy x-ray image data.

5. A method as claimed in claim 1 comprising producing said low-energy x-ray image data and said high-energy x-ray image data and said dual energy x-ray image data as two-dimensional image data.

6. A method as claimed in claim 1 comprising producing said low-energy x-ray image data and said high-energy x-ray image data and said dual energy x-ray image data as three-dimensional image data.

7. An x-ray system comprising:
- an x-ray source that emits x-rays;
- a radiation detector that detects the x-rays emitted by said x-ray source;
- a single x-ray filter consisting essentially of titanium and having a thickness in a range between 0.5 and 1.2 mm; and
- a computerized control and evaluation system configured to operate said x-ray source and said radiation detector to irradiate a subject with x-rays with an x-ray voltage in a range from 20 to 35 kVp, while filtering said x-rays with said single filter consisting essentially of titanium and said single filter having a thickness in a range between 0.5 and 1.2 mm, to produce low-energy x-ray image data of a volume segment of the subject, and to operate said x-ray source and said radiation detector to irradiate the subject with x-rays with an x-ray voltage in a range from 40 to 50 kVp, while filtering said x-rays with said single filter consisting essentially of titanium and said single filter having a thickness in a range between 0.5 and 1.2 mm, to produce high-energy x-ray image data of said volume segment, and to subtract said low-energy x-ray image data from said high-energy x-ray image data to produce dual energy x-ray image data, and to make said dual energy x-ray image data available in electronic form at an output of said control and evaluation system.

8. An x-ray system as claimed in claim 7 wherein said x-ray source and said radiation detector from an x-ray tomosynthesis system, and wherein said control and evaluation system is configured to:
- operate said x-ray tomosynthesis system by implementing a tomosynthesis scan wherein said segment of said subject is irradiated with x-rays from a plurality of successive angle settings;
- for each of said angle settings, operate said x-ray tomosynthesis system to produce said low-energy x-ray image data and to produce said high-energy x-ray image data; and
- for each of said angle settings, produce a dual energy x-ray image by subtracting the low-energy x-ray image data produced at the respective angle setting from the high-energy x-ray image data produced at the respective angle setting.

9. An x-ray system as claimed in claim 8 wherein said control and evaluation unit is configured to operate said x-ray tomosynthesis system to irradiate the volume segment of the subject with x-rays to produce said low-energy x-ray image data and said high-energy x-ray image data for the respective angle setting before moving said x-ray tomosynthesis image system to a next successive angle setting.

10. An x-ray system as claimed in claim 7 wherein said x-ray source and said radiation detector is an x-ray tomosynthesis image system, and wherein said control and evaluation system is configured to:
- operate said x-ray tomosynthesis image system in a tomosynthesis scan to produce said low-energy x-ray image data and said high-energy x-ray image data in alternation with continuous movement of said x-ray source in said tomosynthesis scan; and
- subtract respectively alternating low-energy x-ray image data from respectively alternating high-energy x-ray image data to produce said dual energy x-ray image data.

11. An x-ray system as claimed in claim 7 wherein said control and evaluation system is configured to operate said x-ray source and said radiation detector to produce said low-energy x-ray image data and said high-energy x-ray image data and said dual energy x-ray image data as two-dimensional image data.

12. An x-ray system as claimed in claim 7 wherein said control and evaluation system is configured to operate said x-ray source and said radiation detector to produce said low-energy x-ray image data and said high-energy x-ray image data and said dual energy x-ray image data as three-dimensional image data.

13. A non-transitory, computer-readable data storage medium encoded with programming instructions, said data storage medium being loaded into a computerized control and evaluation system of an x-ray system that comprises an x-ray filter consisting essentially of titanium, said programming instructions causing said computerized control and evaluation system to:
- operate said x-ray system to irradiate a subject with x-rays with an x-ray voltage in a range from 20 to 35 kVp, while filtering said x-rays with a single filter consisting essentially of titanium and said single filter having a thickness in a range between 0.5 and 1.2 mm, to produce low-energy x-ray image data of a volume segment of the subject;
- also operate said x-ray system to irradiate the subject with x-rays with an x-ray voltage in a range from 40 to 50 kVp, while filtering said x-rays with said single filter consisting essentially of titanium and said single filter having a thickness in a range between 0.5 and 1.2 mm, to produce high-energy x-ray image data of said volume segment; and
- subtract said low-energy x-ray image data from said high-energy x-ray image data to produce dual energy x-ray image data, and make said dual energy x-ray image data available in electronic form at an output of said control and evaluation system.

14. A data storage medium as claimed in claim 13 wherein said x-ray system is an x-ray tomosynthesis system, and wherein said programming instructions cause said control and evaluation system to:
- operate said x-ray tomosynthesis system by implementing a tomosynthesis scan wherein said segment of said subject is irradiated with x-rays from a plurality of successive angle settings;
- for each of said angle settings, operate said x-ray tomosynthesis system to produce said low-energy x-ray image data and to produce said high-energy x-ray image data; and
- for each of said angle settings, produce a dual energy x-ray image by subtracting the low-energy x-ray image data produced at the respective angle setting from the high-energy x-ray image data produced at the respective angle setting.

15. A data storage medium as claimed in claim 14 wherein said programming instructions cause said control and evaluation system to irradiate the volume segment of the subject with x-rays to produce said low-energy x-ray image data and said high-energy x-ray image data for the respective angle setting before moving said x-ray tomosynthesis image system to a next successive angle setting.

16. A data storage medium as claimed in claim 13 wherein said x-ray image system is an x-ray tomosynthesis image system, and wherein said programming instructions cause said control and evaluation system to:
- operate said x-ray tomosynthesis image system in a tomosynthesis scan to produce said low-energy x-ray image data and said high-energy x-ray image data in alternation with continuous movement of said x-ray source in said tomosynthesis scan; and subtract respectively alternating low-energy x-ray image data from respectively alternating high-energy x-ray image data to produce said dual energy x-ray image data.

17. A data storage medium as claimed in claim 13 wherein said programming instructions cause said control and evaluation system to operate said x-ray system to produce said low-energy x-ray image data and said high-energy x-ray image data and said dual energy x-ray image data as two-dimensional image data.

18. A data storage medium as claimed in claim 13 wherein said programming instructions cause said control and evaluation system to operate said x-ray system to produce said low-energy x-ray image data and said high-energy x-ray image data and said dual energy x-ray image data as three-dimensional image data.

* * * * *